A method of forming a surface mount transformer. The
(12) United States Patent
Iverson et al.

(10) Patent No.: US 6,927,663 B2
(45) Date of Patent: Aug. 9, 2005

(54) FLYBACK TRANSFORMER WIRE ATTACH METHOD TO PRINTED CIRCUIT BOARD

(75) Inventors: Tom Iverson, Brooklyn Park, MN (US); Bart Carey, Roseville, MN (US); Robert S. Harguth, Ham Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 33 days.

(21) Appl. No.: 10/625,827

(22) Filed: Jul. 23, 2003

(65) Prior Publication Data

US 2005/0017054 A1 Jan. 27, 2005

(51) Int. Cl.[7] ................................................. H01F 5/00
(52) U.S. Cl. ........................ 336/200; 336/192; 336/232; 336/223; 29/602.1
(58) Field of Search ................................. 336/192, 200, 336/223, 232, 198, 212, 183, 96; 29/602.1, 606

(56) References Cited

U.S. PATENT DOCUMENTS 6,211,767 B1 * 4/2001 Jitaru ......................... 336/200
6,664,883 B2 * 12/2003 Patel et al. ................. 336/200
6,820,321 B2 * 11/2004 Harding ..................... 29/602.1

* cited by examiner

*Primary Examiner*—Anh Mai
(74) *Attorney, Agent, or Firm*—Schwegman, Lundberg, Woesser & Kluth, P.A.

(57) ABSTRACT

A method of forming a surface mount transformer. The method comprises winding insulated wire around a magnetic core to form at least one secondary transformer coil, winding insulated wire around the magnetic core to form at least one primary transformer coil, attaching wire ends of the at least one primary coil to at least first and second vias of a printed circuit board (PCB), attaching wire ends of the at least one secondary coil to at least third and fourth vias of the PCB, affixing the coils and the magnetic core to the first side of the PCB, and attaching the coil wire ends flush to a surface of the vias on the second side of the PCB.

22 Claims, 6 Drawing Sheets

FLYBACK TRANSFORMER WIRE ATTACH METHOD TO PRINTED CIRCUIT BOARD

TECHNICAL FIELD

This document relates to flyback transformers, and in particular, to a surface mountable flyback toroidal transformer for use in an implantable medical device.

BACKGROUND

Flyback transformers are used with flyback power converters to provide electrical isolation between the power source and load. The transformers are comprised of primary windings and secondary windings around a common core of magnetic material. The voltage produced in the secondary winding is related to the voltage in the primary winding by the ratio of turns between the primary and secondary windings. In a toroidal transformer, the windings are formed around a toroid-shaped core.

It is important to minimize the size of components, including transformers, used in implantable medical devices to reduce the overall size of the implantable device for patient comfort. Also, because implantable devices are generally battery powered it is important to use battery power efficiently by reducing losses due to resistance and thereby extend the battery life.

Miniaturized transformers are often formed by forming the windings around a bobbin to hold the wires and a core is then slipped into the bobbin. Often, the windings are formed around the toroid-shaped core. The bobbin and/or core are placed in a package with the winding wires wrapped around package leads. The packaged transformer is then mounted onto a main circuit board. The package leads add height to the final transformer assembly. Also, the leads add resistance to the transformer assembly and the efficiency of the transformer is reduced by the energy loss resulting from the lead resistance. What is needed is a transformer assembly that reduces or eliminates the disadvantages of using a transformer assembly that includes leads.

SUMMARY

This document discusses a surface mountable toroidal transformer and a method for making the transformer. The transformer comprises a toroid-shaped core comprising magnetic material, at least one primary coil of insulated wire wound around the core where the primary coil is electrically isolated from a transformer load, at least one secondary coil of insulated wire wound around the core, and a printed circuit board (PCB) where the PCB includes a plurality of vias in communication with bonding pads. Wire ends of the at least one primary and at least one secondary coils are attached to the vias and the toroid-shaped core and coils are affixed to the PCB such that a center axis of the toroid is substantially perpendicular to the PCB.

The method of forming a transformer comprises winding insulated wire around a magnetic core to form at least one secondary transformer coil, winding insulated wire around the magnetic core to form at least one primary transformer coil, attaching wire ends of the at least one primary coil to at least first and second vias of a PCB, attaching wire ends of the at least one secondary coil to at least third and fourth vias of the PCB, affixing the coils and the magnetic core to the first side of the PCB, and attaching the coil wire ends flush to a surface of the vias on the second side of the PCB.

This summary is intended to provide an overview of the subject matter of the present application. It is not intended to provide an exclusive or exhaustive explanation of the invention. The detailed description is included to provide further information about the subject matter of the preset patent application.

BRIEF DESCRIPTION OF THE DRAWINGS

In the drawings like numerals refer to like components throughout the several views.

DETAILED DESCRIPTION

In the following detailed description, reference is made to the accompanying drawings which form a part hereof, and specific embodiments in which the invention may be practiced are shown by way of illustration. It is to be understood that other embodiments may be used and structural changes may be made without departing from the scope of the present invention.

Figure 1:
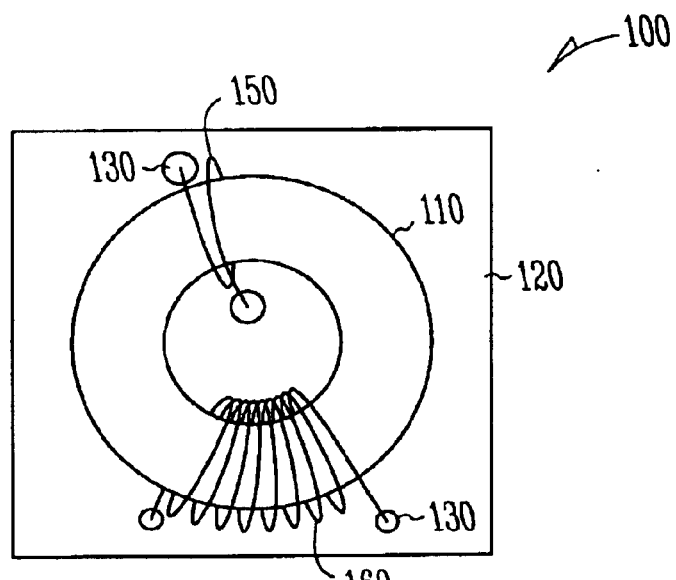
FIG. 1 is a drawing of a toroidal transformer mounted on a printed circuit board (PCB).

As stated previously, this document discusses a surface mountable toroidal transformer and a method for making the transformer. FIG. 1 is a drawing of an embodiment of a toroidal transformer 100. A toroid-shaped core of magnetic material 110 is mounted on a printed circuit board (PCB) 120. In one embodiment, the PCB is FR4. In another embodiment, the PCB comprises ceramic material. In a further embodiment, the PCB comprises flexible circuit tape. The center axis of the core 110 is substantially perpendicular to the plane of the PCB 120. In one embodiment, the core is a molypermalloy core. In another or the same embodiment, the core is mounted on the PCB using epoxy. The PCB includes vias 130. FIG. 1 also shows simplified drawings of a primary coil 150 and a secondary coil 160 comprised of insulated wire wound around the core 110. The coils 150, 160 are attached to vias 130 by soldering.

Figure 2:
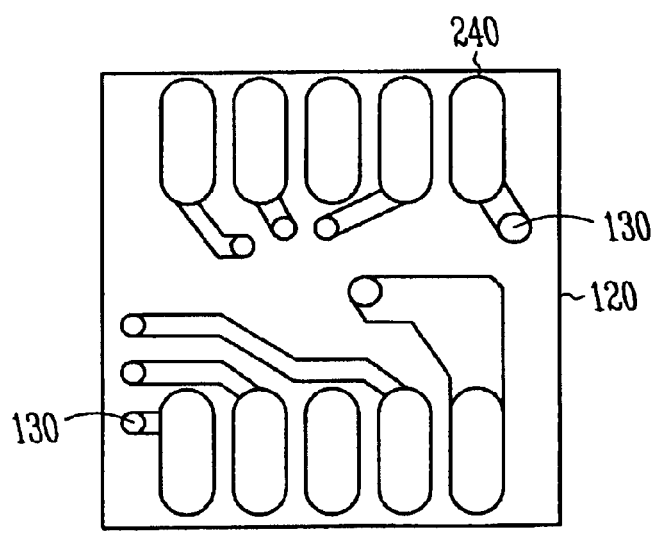
FIG. 2 is a drawing of a PCB used with a toroidal transformer showing vias and bonding pads.

FIG. 2 shows a second side of the PCB 120. The vias 130 are in communication with bonding pads 240. The bonding pads 240 are then bonded to a main circuit board. Thus the transformer assembly eliminates package leads and reduces the height of the assembly.

Figure 3:
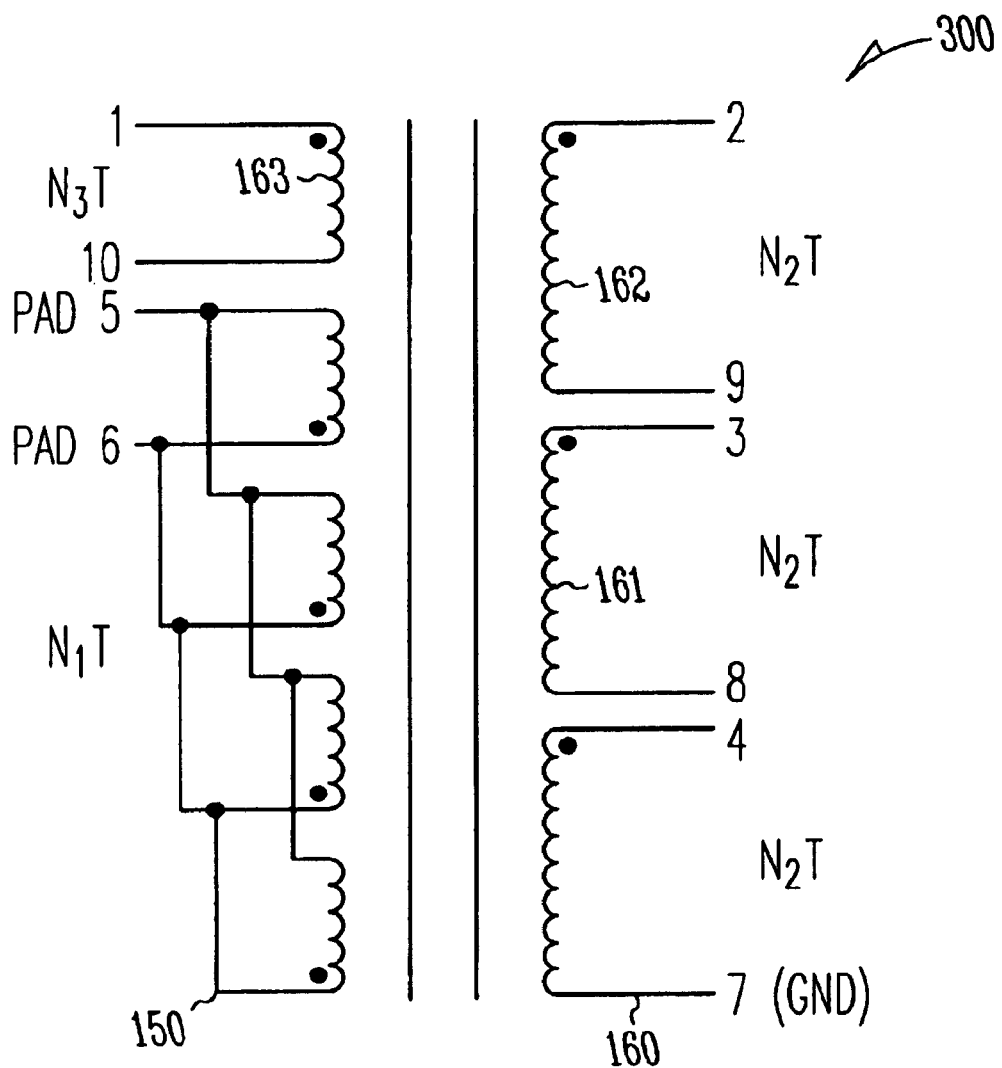
FIG. 3 is an electrical schematic of a transformer using multiple primary and secondary coil windings.

The simplified drawing of FIG. 1 shows only 4 vias 130 of the PCB 120 being used. Additional vias 130 are used to accommodate additional windings. FIG. 3 shows an electrical schematic 300 of a transformer using multiple primary and secondary coil windings 150, 160. In the embodiment shown in the schematic, the primary coil 150 is comprised of four windings of $N_1$ turns (T) electrically connected in parallel to vias in communication with bonding pads five and six of the PCB. Connecting the windings in parallel reduces the net resistance of the primary coil 150. In another embodiment, the resistance is further reduced by using a heavier gauge wire to form the primary windings. In an example of this embodiment, the wire used in the primary coil is 30 AWG and the wire in the secondary coil is 42 AWG. In another embodiment, the net resistance is 15 milliohms. Thus the assembly increases the efficiency of the transformer by reducing the resistance of primary coil 150 and by eliminating the use of package leads in the assembly.

The finished transformer assembly is then connected to a higher level assembly of an electronic device. In one embodiment, the bonding pads of the transformer are solder-bumped. The transformer is then surface mounted to the higher level assembly by placing the bonding pads in position and reflowing the solder to make an electrical connection. The solder used for solder bumping is different than the solder used for attaching the coil ends. The solder used for bumping has a lower melting temperature so that the solder used to attach the vias does not melt and reflow while the transformer PCB is being attached to the higher level assembly. In another embodiment, the bonding pads are on the same side of the PCB as the toroid and the electrical connection to the higher level assembly is made by wire bonding the transformer to pads of the higher level assembly.

The schematic in FIG. 3 also shows multiple secondary coils 160, 161, 162 and 163. The ends of each of the coils are attached to vias 130 of the PCB 120. Thus four voltages related to the ratio of turns between the primary coil 150 and secondary coils 160, 161, 162, 163 are available on the PCB. In the embodiment shown, coils 160, 161 and 162 are comprised of $N_2$ turns and coil 163 is comprised of $N_3$ turns. Thus it is not necessary for all of the secondary coils to be identical and different voltage magnitudes are available on the secondary coils 160, 161, 162, and 163. Also, the dot references of the secondary coils 160, 161, 162, 163 in the schematic indicate that the winding orientation of the secondary coils is different from the primary windings 150. This is accomplished, for example, by orienting the primary windings clockwise and the secondary windings counterclockwise. One of ordinary skill in the art would understand, upon reading and comprehending this disclosure, that various embodiments of the primary and secondary coils 150, 160 include various combinations of windings, winding turns, winding orientations and electrical connections.

Figure 4:
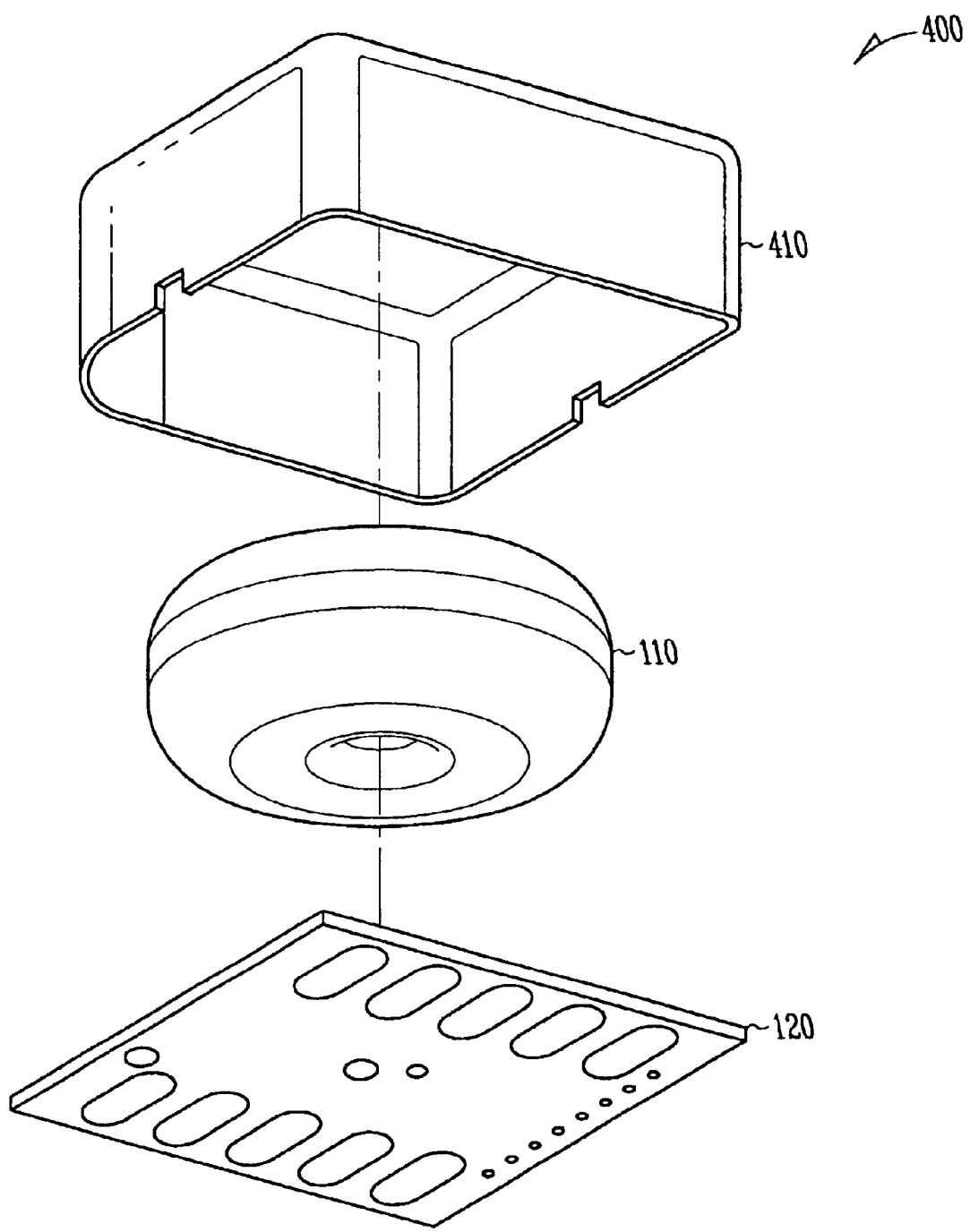
FIG. 4 is an exploded view of a PCB, a toroid-shaped core and a cover.

FIG. 4 is an exploded view of an embodiment of a transformer assembly 400 that includes a cover 410. In one embodiment, the cover 410 is plastic. In another embodiment, the cover 410 includes an electrically conductive material another embodiment, the cover 410 of electrically conductive material is connected to a DC voltage level, such as electrical ground for example, to form an electromagnetic shield. Shielding the transformer reduces electromagnetic interference within the medical device if the transformer is used in a flyback power converter circuit.

Figure 5:
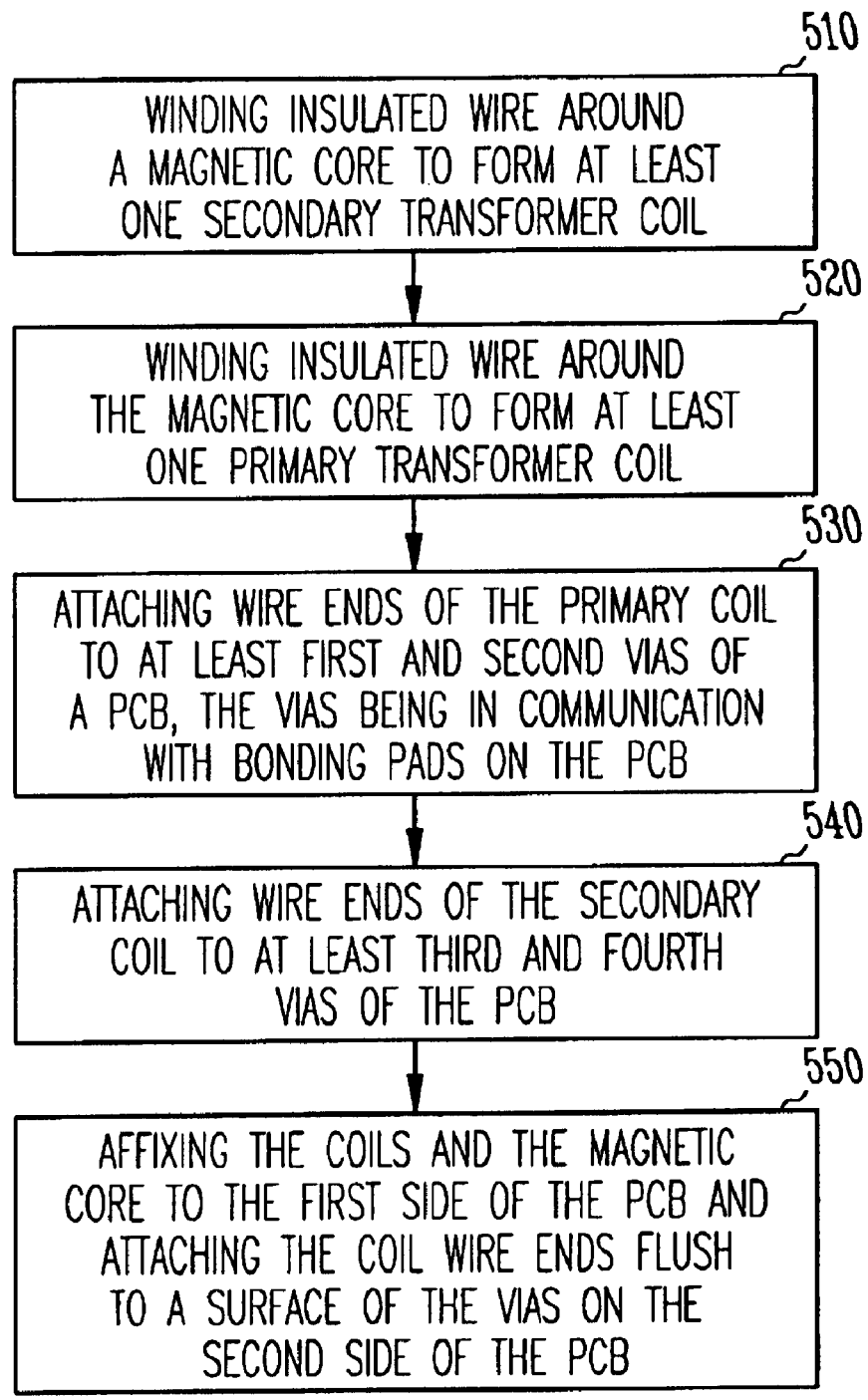
FIG. 5 is a flow chart of a method of forming a transformer.

FIG. 5 is a flow chart of a method of forming a transformer. At 510, insulated wire is wound around a magnetic core to form at least one secondary transformer coil. At 520, insulated wire is wound around the magnetic core to form at least one primary transformer coil, the primary coil electrically isolated from a transformer load. At 530, wire ends of the at least one primary coil are attached to at least first and second vias of a printed circuit board (PCB), the PCB having a first and second side, the vias being in communication with bonding pads on the PCB. At 540, wire ends of the at least one secondary coil are attached to at least third and fourth vias of the PCB. At 550, the coils and the magnetic core are affixed to the first side of the PCB and the coil wire ends are attached flush to a surface of the vias on the second side of the PCB.

In one embodiment, attaching wire ends flush to a surface of the vias of the PCB includes, inserting the primary and secondary coil wire ends into vias, cutting the wire ends to length, and soldering the wire ends to the vias. In another embodiment, the wire ends are cut to extend about one-eighth of an inch beyond the board after soldering. The coil ends are then ground flush to the surface. In another embodiment, soldering the wire ends to the vias includes melting the insulation off of the wire ends as the ends are soldered.

Figure 6:
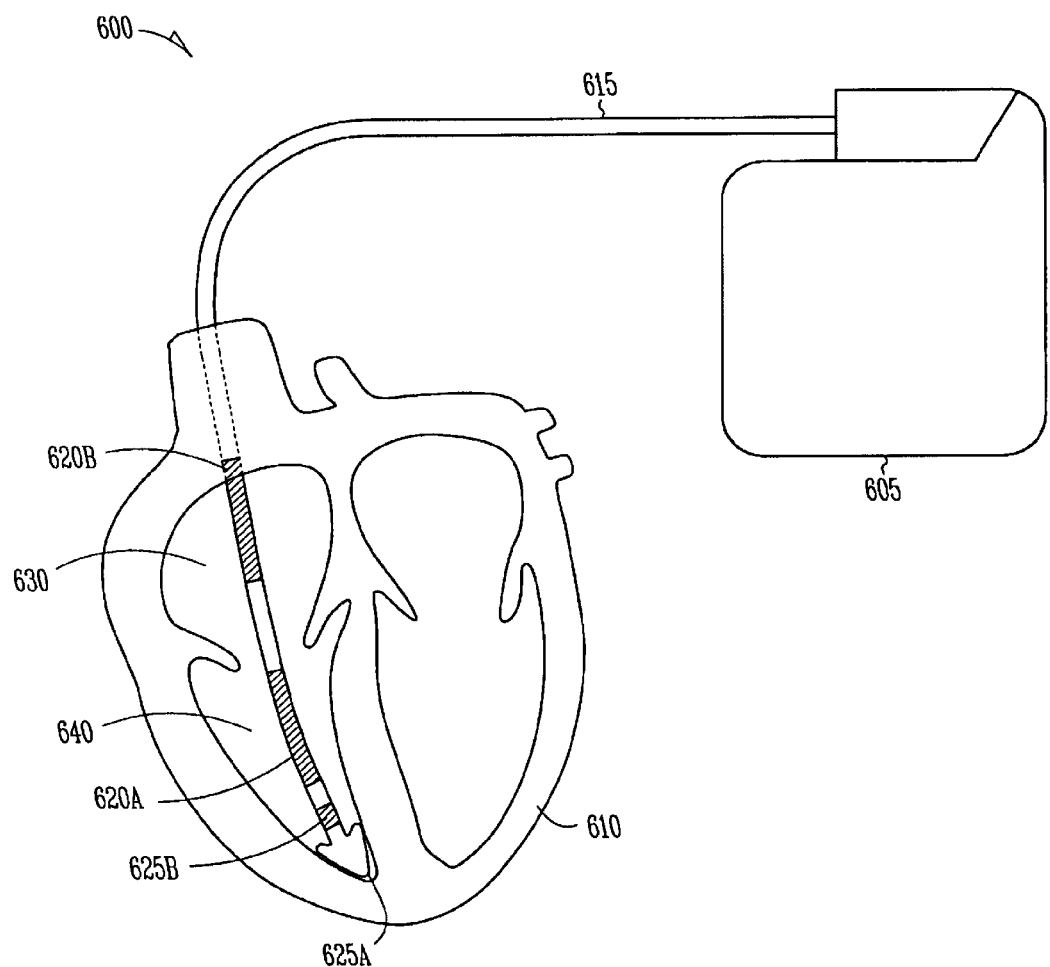
FIG. 6 is a generalized schematic diagram of one embodiment of a portion of a cardiac rhythm management system 600.

FIG. 6 is a generalized schematic diagram of one embodiment of a portion of a cardiac rhythm management system 600. Various embodiments of system 600 include external or implantable pulse generators, pacer/defibrillators, cardioverters, defibrillators, any combination of the foregoing, or any other system using or maintaining cardiac rhythms.

In the embodiment of FIG. 6, cardiac rhythm management system 600 includes an implantable pulse generator 605 coupled to heart 610 via one or more endocardial or epicardial leads, such as a pacing lead or a defibrillation lead 615. Defibrillation lead 615 includes one or more defibrillation electrodes, such as for delivering defibrillation counter-shock ("shock") therapy via first defibrillation electrode 620A and/or second defibrillation electrode 620B. Defibrillation lead 615 may also include additional electrodes, such as for delivering pacing therapy via first pacing electrode 625A (e.g., a "tip" electrode) and/or second pacing electrode 625B (e.g., a "ring" electrode). Defibrillation electrodes 620A–B and pacing electrodes 625A–B are typically disposed in or near one or more chambers of heart 610.

Figure 7:
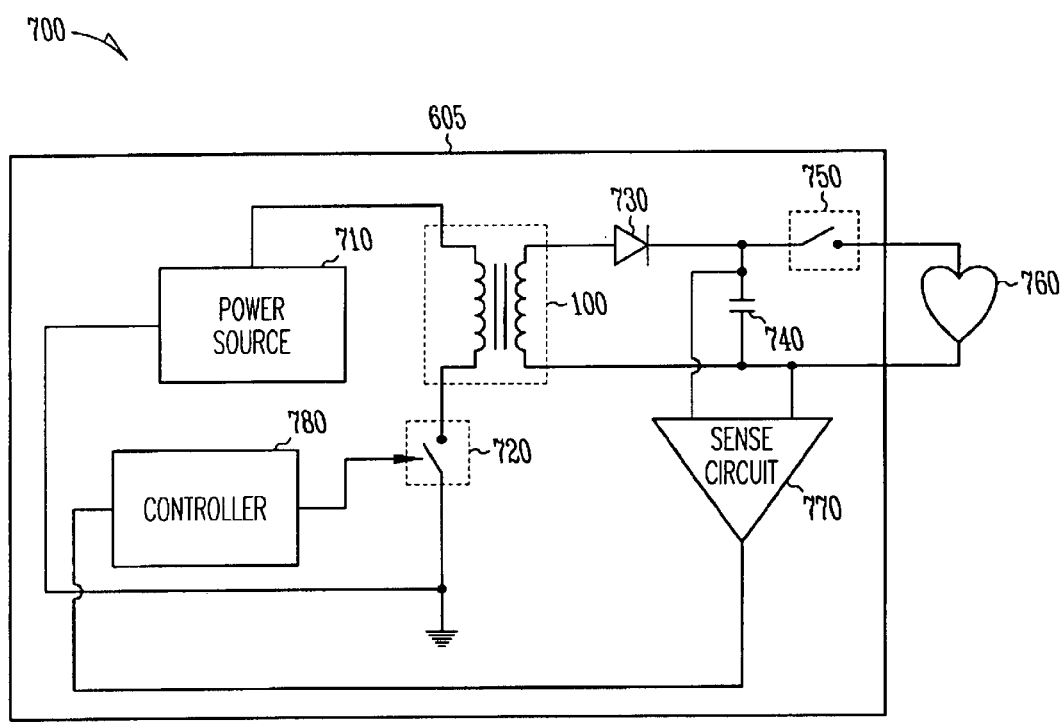
FIG. 7 shows a generalized schematic of one embodiment of a voltage generator used in an implantable pulse generator.

FIG. 7 shows a schematic of an embodiment of a voltage generator 700 used in an implantable pulse generator 605 that includes an implantable cardioverter defibrillator (ICD). The voltage generator 700 uses a transformer 100 mounted on a circuit board. The voltage generator 700 includes a power source 710 having output terminals. Across the terminals of the power source 710 is a circuit board mounted non-lead transformer 100 connected to a main circuit board of the ICD and a switch 720 connected in series with the primary coil of the transformer 100. Diode 730 is connected in series with the secondary coil of transformer 100 across the terminals of a load. The load includes a capacitive storage element 740 connected by switch 750 to leads adaptable for connection to a heart 760. Switch 750 is closed to deliver the energy stored in the capacitive element to the heart 760 to perform cardioversion. Sense circuit 770 monitors the voltage of the capacitive element. In one embodiment, the sense circuit 770 is a comparator and a known voltage reference.

The topology of the voltage generator 700 shown is a flyback voltage converter. When switch 720 is closed, diode 730 is reverse biased and energy from the power source 710 is delivered to the transformer through the primary winding, storing energy in the core of the transformer 100. When switch 720 is opened, diode 730 becomes forward biased and energy stored in the core is delivered to the capacitive load 740. The voltage transfer from the power source 710 to the load 740 is dependent on the duty ratio of the switch 720. The output signal of the sense circuit 770 is connected to controller 780. When the voltage of the capacitive element 740 is below a selected threshold voltage, the sense circuit 770 signals the controller to deliver energy from the power source by repeatedly cycling switch 720. When the output voltage of the power the selected threshold voltage the sense circuit 770 signals the controller 780 to open the switch 720. The switching methodology used to charge the transformer shows the advantage of minimizing the resistance of the primary coil to increase the efficiency of the transformer.

Although specific examples have been illustrated and described herein, it will be appreciated by those of ordinary skill in the art that any arrangement calculated to achieve the same purpose could be substituted for the specific example shown. This application is intended to cover any adaptations or variations of the present invention. Therefore, it is intended that this invention be limited only by the claims and their legal equivalents.

What is claimed is:

1. A transformer comprising:
   a toroid-shaped core comprising magnetic material;
   at least one primary coil of insulated wire wound around the core, the primary coil electrically isolated from a transformer load;
   at least one secondary coil of insulated wire wound around the core; and
   a printed circuit board (PCB), wherein the PCB includes a plurality of vias and bonding pads, the vias in communication with the bonding pads, and wherein wire ends of the at least one primary and at least one secondary coils are attached to the vias, the toroid-shaped care and coils affixed to the PCB such that a center axis of the toroid is substantially perpendicular to the PCB.

2. The transformer of claim 1, wherein the at least one primary coil comprises a plurality of windings electrically connected in parallel to each other.

3. The transformer of claim 2, wherein first ends of the plurality of windings are attached to a first via and second ends of the plurality of wires are attached to a second via.

4. The transformer of claim 3, wherein an electrical resistance of the primary coil is about 15 milliohms.

5. The transformer of claim 4, wherein the at least one secondary coil has a different number of windings than the at least one primary coil.

6. The transformer of claim 5, wherein the at least one secondary coil is a plurality of coils, wherein at least two of the plurality of coils have a different number of turns.

7. The transformer of claim 6, wherein the at least one primary coil comprises wire of 30 American wire gauge (AWG) and the at least one secondary wire comprises wire of 42 AWG.

8. The transformer of claim 6, wherein the transformer further includes a cover over the coils.

9. The transformer of claim 8, wherein the cover comprises an electrically conductive material.

10. The transformer of claim 9, wherein the cover is electrically connected so as to provide an electromagnetic shield to the transformer.

11. A method of forming a transformer comprising:
    winding insulated wire around a magnetic core to form at least one secondary transformer coil;
    winding insulated wire around the magnetic core to form at least one primary transformer coil, the primary coil electrically isolated from a transformer load;
    attaching wire ends of the at least one primary coil to at least first and second vias of a printed circuit board (PCB), the vias being in communication with bonding pads on the PCB;
    attaching wire ends of the at least one secondary coil to at least third and fourth vias of the PCB; and
    attaching the wire ends of the primary and secondary coils flush to a surface of the vias on the PCB.

12. The method of claim 11, wherein attaching wire ends of the primary and secondary coils to vias of the PCB includes:
    inserting the primary and secondary coil wire ends into vias;
    soldering the wire ends of the primary and secondary coils to the vias; and
    cutting the wire ends of the primary and secondary coils to length.

13. The method of claim 12, wherein the method further includes grinding the wire ends of the primary and secondary coils flush to the surface.

14. The method of claim 12, wherein soldering the wire ends of the primary and secondary coils includes melting insulation from the wire ends.

15. The method of claim 11, wherein forming at least one secondary coil includes forming a plurality of secondary coils, at least two of the secondary coils having a different number of turns.

16. The method of claim 11, wherein forming at least one primary coil includes forming a plurality of primary coils.

17. The method of claim 16, wherein forming a plurality of primary coils includes electrically connecting the primary coils in parallel.

18. The method of claim 11, further comprising affixing the coils and the magnetic core to a first side of the PCB with epoxy.

19. The method of claim 18, wherein the method further includes covering the coils and the magnetic core with an electromagnetic shield.

20. A method comprising:
    attaching wire ends of at least one primary coil of a transformer to at least first and second vias of a printed circuit board (PCB), the vias being in communication with bonding pads on the PCB;
    attaching wire ends of at least one secondary coil of a transformer to at least third and fourth vias of the PCB; and
    attaching the wire ends of the primary and secondary coils flush to a surface of the vias on the PCB.

21. The method of claim 20, wherein attaching wire ends of the transformer primary and secondary coils to vias of the PCB includes:
    inserting the primary and secondary coil wire ends into vias; and
    soldering the wire ends of the primary and secondary coils to the vias.

22. The method of claim 21, the method further including trimming the wire ends of the primary and secondary coils.

* * * * *

UNITED STATES PATENT AND TRADEMARK OFFICE
CERTIFICATE OF CORRECTION

PATENT NO. : 6,927,663 B2
DATED : August 9, 2005
INVENTOR(S) : Iverson et al.

It is certified that error appears in the above-identified patent and that said Letters Patent is hereby corrected as shown below:

Title page,
Item [74], *Attorney, Agent, or Firm*, delete "Woesser" and insert -- Woessner --.

Column 5,
Line 25, delete "care" and insert -- core --.

Signed and Sealed this

Third Day of January, 2006

JON W. DUDAS
*Director of the United States Patent and Trademark Office*